United States Patent [19]

Svendsen et al.

[11] Patent Number: 6,074,863
[45] Date of Patent: Jun. 13, 2000

[54] *C. ANTARCTICA* LIPASE VARIANTS

[75] Inventors: Allan Svendsen, Birkerød; Shamkant Anant Pathar, Lyngby; Michi Egel-Mitani, Vedbæk; Kim Borch, Copenhagen; Ib Groth Clausen, Hillerød; Mogens Trier Hansen, Lynge, all of Denmark

[73] Assignee: Novo Nordisk A/S, Bagsvaerd, Denmark

[21] Appl. No.: 08/360,758

[22] PCT Filed: Jul. 5, 1993

[86] PCT No.: PCT/DK93/00225

§ 371 Date: Dec. 22, 1994

§ 102(e) Date: Dec. 22, 1994

[87] PCT Pub. No.: WO94/01541

PCT Pub. Date: Jan. 20, 1994

[30] Foreign Application Priority Data

Jul. 6, 1992 [DK] Denmark .................................. 0888/92

[51] Int. Cl.[7] .............................. C12N 9/20; C12N 15/63; C12P 7/64; C07H 21/04
[52] U.S. Cl. ................... 435/198; 435/252.3; 435/320.1; 435/134; 536/23.2
[58] Field of Search ................................ 435/198, 320.1, 435/252.3, 254.2, 254.3, 134, 267; 536/23.2

[56] References Cited

FOREIGN PATENT DOCUMENTS

| 0 305 216 A1 | 8/1988 | European Pat. Off. . |
| 0 318 775 A2 | 11/1988 | European Pat. Off. . |
| 0 407 225 | 7/1990 | European Pat. Off. . |
| 0 451 452 A1 | 2/1991 | European Pat. Off. . |
| 88/02775 | 4/1988 | WIPO . |
| 8802775 | 4/1988 | WIPO . |
| 9015868 | 12/1990 | WIPO . |
| 92/05249 | 4/1992 | WIPO . |

OTHER PUBLICATIONS

Aoyama et al., Federation of European Biochemical Societies, vol. 242, No. 1, pp. 36–40, (1988).
Baba et al., Biochemistry, vol. 30, pp. 500–510, (1991).
Bodmer et al., Biochimica et Biophysica Acta, vol. 909, pp. 237–244, (1987).
Caro et al., Biochimica et Biophysica Acta, vol. 671, pp. 129–138, 1981.
Datta et al., J. Biol. Chem., vol. 263, No. 3, pp. 1107–1110, (1988).
Docherty et al., Nucleic Acids Research, vol. 13, No. 6, pp. 1891–1903, (1985).
Grusby et al., Cell 60, 451–59, (1990).
Komaromy et al., Proc.Natl.Acad.Sci., vol. 84, pp. 1526–1530, (1987).
Lowe et al., J.Biol.Chem., vol. 264, No. 33, pp. 20042–20048, (1989).
Mickel et al., J.Biol.Chem., vol. 264, No. 22, pp. 12895–12901, 1989.
Derewenda et al., Biochemistry and Cell Biology, (1992).
Derewenda et al., Biochem., vol. 31, pp. 1532–1541, (1992).
Schrag et al., Nature, vol. 351, pp. 761–764, (1991).
Winkler et al., Nature, vol. 343, pp. 771–774, (1990).
Brzozowski et al., Nature, vol. 351, pp. 491–494, (1991).
Brady et al., Nature, vol. 343, pp. 767–770, (1990).
Patkar et al., Chemical Abstracts, vol. 118, No. 9, p. 321, 1993.
JP 1–225481, Sep. 8, 1989, Abstract, vol. 13, No. 549, C–662.
Ibrahim et al., Chemical Abstracts, vol. 106, No. 21, 25, p. 310, 1987.
Kosugi et al., Chemical Abstracts, vol. 76, No. 13, 720327, p. 267, 1972.
Sugihara et al., Chemical Abstracts, vol. 118, No. 1, p. 301, 1993.
Dichek, H.L. et al. (1991) "Identification of two separate allelic mutations in the lipoprotein lipase gene of a patient with the familial hyperchylomicronemia syndrome" *J. Biol. Chem.* 266(1):473–477.
Emmerich, J. et al. (1992) "Human lipoprotein lipase" *J. Biol. Chem.* 267(6):4161–4165.
Chiba, H. et al. (1973) "Roles of tryptophan residues on the *Rhizopus delemar* lipase activity: chemical modificaiton in a water–olive oil emulsion" *Biochim. Biophys. Acta* 327(2):380–392.
Liu, W.–H. et al. (1977) "The chemical modification of the lipase of *Humicola lanuginosa* by N–bromosuccinimide in urea solution" *Agric. Biol. Chem.* 41(1):131–135.

*Primary Examiner*—Robert A. Wax
*Assistant Examiner*—Kawai Lau
*Attorney, Agent, or Firm*—Steve T. Zelson, Esq.; Valeta Gregg, Esq.

[57] ABSTRACT

A lipase variant of a parent lipase comprising a trypsin-like catalytic triad including an active serine located in a predominantly hydrophobic, elongated binding pocket of the lipase molecule and, located in a critical position of a lipid contact zone of the lipase structure, an amino acid residue different from an aromatic amino acid residue, which amino acid residue interacts with a lipid substrate at or during hydrolysis, in which lipase variant said amino acid residue has been replaced by an aromatic amino acid residue so as to confer to the variant an increased specific activity as compared to that of the parent lipase. The parent lipase may be a *C. antarctica* lipase A essentially free from other substances from *C. antarctica*, which comprises the amino acid sequence shown in SEQ ID No. 2, or a variant of said lipase which (1) has lipase activity, (2) reacts with an antibody reactive with at least one epitope of *C. antarctica* lipase A having th eamino acid sequence SEQ ID No. 2, and/or (3) is encoded by a nucleotide sequence which hybridizes with an oligonucleotide probe prepared on the basis of the full or partial nucleotide sequence shown in SEQ ID No. 1 encoding the *C. antarctica* lipase A.

28 Claims, 3 Drawing Sheets

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1329 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GCGGCTCCGG CGGCCGAGAC GCTGGACCGA CGGGCGGCGC TGCCCAACCC CTACGACGAT    60

```
CCCTTCTACA CGACGCCATC CAACATCGGC ACGTTTGCCA AGGGCCAGGT GATCCAATCT      120

CGCAAGGTGC CCACGGACAT CGGCAACGCC AACAACGCTG CGTCGTTCCA GCTGCAGTAC      180

CGCACCACCA ATACGCAGAA CGAGGCGGTG GCCGACGTGG CCACCGTGTG GATCCCGGCC      240

AAGCCCGCTT CGCCGCCCAA GATCTTTTCG TACCAGGTCT ACGAGGATGC CACGGCGCTC      300

GACTGTGCTC CGAGCTACAG CTACCTCACT GGATTGGACC AGCCGAACAA GGTGACGGCG      360

GTGCTCGACA CGCCCATCAT CATCGGCTGG GCGCTGCAGC AGGGCTACTA CGTCGTCTCG      420

TCCGACCACG AAGGCTTCAA AGCCGCCTTC ATCGCTGGCT ACGAAGAGGG CATGGCTATC      480

CTCGACGGCA TCCGCGCGCT CAAGAACTAC CAGAACCTGC CATCCGACAG CAAGGTCGCT      540

CTTGAGGGCT ACAGTGGCGG AGCTCACGCC ACCGTGTGGG CGACTTCGCT TGCTGAATCG      600

TACGCGCCCG AGCTCAACAT TGTCGGTGCT TCGCACGGCG GCACGCCCGT GAGCGCCAAG      660

GACACCTTTA CATTCCTCAA CGGCGGACCC TTCGCCGGCT TTGCCCTGGC GGGTGTTTCG      720

GGTCTCTCGC TCGCTCATCC TGATATGGAG AGCTTCATTG AGGCCCGATT GAACGCCAAG      780

GGTCAGCGGA CGCTCAAGCA GATCCGCGGC CGTGGCTTCT GCCTGCCGCA GGTGGTGTTG      840

ACCTACCCCT TCCTCAACGT CTTCTCGCTG GTCAACGACA CGAACCTGCT GAATGAGGCG      900

CCGATCGCTA GCATCCTCAA GCAGGAGACT GTGGTCCAGG CCGAAGCGAG CTACACGGTA      960

TCGGTGCCCA AGTTCCCGCG CTTCATCTGG CATGCGATCC CCGACGAGAT CGTGCCGTAC     1020

CAGCCTGCGG CTACCTACGT CAAGGAGCAA TGTGCCAAGG GCGCCAACAT CAATTTTTCG     1080

CCCTACCCGA TCGCCGAGCA CCTCACCGCC GAGATCTTTG GTCTGGTGCC TAGCCTGTGG     1140

TTTATCAAGC AAGCCTTCGA CGGCACCACA CCCAAGGTGA TCTGCGGCAC TCCCATCCCT     1200

GCTATCGCTG GCATCACCAC GCCCTCGGCG GACCAAGTGC TGGGTTCGGA CCTGGCCAAC     1260

CAGCTGCGCA GCCTCGACGG CAAGCAGAGT GCGTTCGGCA AGCCCTTTGG CCCCATCACA     1320

CCACCTTAG                                                             1329
```

(2) INFORMATION FOR SEQ ID NO: 2:

(i) SEQUENCE CHARACTERISTICS:
        (A) LENGTH: 463 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Arg Val Ser Leu Arg Ser Ile Thr Ser Leu Leu Ala Ala Ala Thr
 1               5                  10                  15

Ala Ala Val Leu Ala Ala Pro Ala Ala Glu Thr Leu Asp Arg Arg Ala
             20                  25                  30

Ala Leu Pro Asn Pro Tyr Asp Asp Pro Phe Tyr Thr Thr Pro Ser Asn
         35                  40                  45

Ile Gly Thr Phe Ala Lys Gly Gln Val Ile Gln Ser Arg Lys Val Pro
     50                  55                  60

Thr Asp Ile Gly Asn Ala Asn Asn Ala Ser Phe Gln Leu Gln Tyr
65                  70                  75                  80

Arg Thr Thr Asn Thr Gln Asn Glu Ala Val Ala Asp Val Ala Thr Val
                 85                  90                  95

Trp Ile Pro Ala Lys Pro Ala Ser Pro Pro Lys Ile Phe Ser Tyr Gln
            100                 105                 110
```

```
Val Tyr Glu Asp Ala Thr Ala Leu Asp Cys Ala Pro Ser Tyr Ser Tyr
        115                 120                 125

Leu Thr Gly Leu Asp Gln Pro Asn Lys Val Thr Ala Val Leu Asp Thr
130                 135                 140

Pro Ile Ile Ile Gly Trp Ala Leu Gln Gln Gly Tyr Tyr Val Val Ser
145                 150                 155                 160

Ser Asp His Glu Gly Phe Lys Ala Ala Phe Ile Ala Gly Tyr Glu Glu
                165                 170                 175

Gly Met Ala Ile Leu Asp Gly Ile Arg Ala Leu Lys Asn Tyr Gln Asn
            180                 185                 190

Leu Pro Ser Asp Ser Lys Val Ala Leu Glu Gly Tyr Ser Gly Gly Ala
            195                 200                 205

His Ala Thr Val Trp Ala Thr Ser Leu Ala Glu Ser Tyr Ala Pro Glu
        210                 215                 220

Leu Asn Ile Val Gly Ala Ser His Gly Gly Thr Pro Val Ser Ala Lys
225                 230                 235                 240

Asp Thr Phe Thr Phe Leu Asn Gly Gly Pro Phe Ala Gly Phe Ala Leu
                245                 250                 255

Ala Gly Val Ser Gly Leu Ser Leu Ala His Pro Asp Met Glu Ser Phe
                260                 265                 270

Ile Glu Ala Arg Leu Asn Ala Lys Gly Gln Arg Thr Leu Lys Gln Ile
        275                 280                 285

Arg Gly Arg Gly Phe Cys Leu Pro Gln Val Val Leu Thr Tyr Pro Phe
290                 295                 300

Leu Asn Val Phe Ser Leu Val Asn Asp Thr Asn Leu Leu Asn Glu Ala
305                 310                 315                 320

Pro Ile Ala Ser Ile Leu Lys Gln Glu Thr Val Val Gln Ala Glu Ala
                325                 330                 335

Ser Tyr Thr Val Ser Val Pro Lys Phe Pro Arg Phe Ile Trp His Ala
            340                 345                 350

Ile Pro Asp Glu Ile Val Pro Tyr Gln Pro Ala Ala Thr Tyr Val Lys
            355                 360                 365

Glu Gln Cys Ala Lys Gly Ala Asn Ile Asn Phe Ser Pro Tyr Pro Ile
370                 375                 380

Ala Glu His Leu Thr Ala Glu Ile Phe Gly Leu Val Pro Ser Leu Trp
385                 390                 395                 400

Phe Ile Lys Gln Ala Phe Asp Gly Thr Thr Pro Lys Val Ile Cys Gly
                405                 410                 415

Thr Pro Ile Pro Ala Ile Ala Gly Ile Thr Thr Pro Ser Ala Asp Gln
                420                 425                 430

Val Leu Gly Ser Asp Leu Ala Asn Gln Leu Arg Ser Leu Asp Gly Lys
            435                 440                 445

Gln Ser Ala Phe Gly Lys Pro Phe Gly Pro Ile Thr Pro Pro Glx
450                 455                 460
```

(2) INFORMATION FOR SEQ ID NO: 3:

(i) SEQUENCE CHARACTERISTICS:
      (A) LENGTH: 277 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 3:

-continued

```
Met Asp Asp Ser Val Asn Thr Arg Tyr Pro Ile Leu Leu Val His Gly
 1               5                  10                  15

Leu Phe Gly Phe Asp Arg Ile Gly Ser His His Tyr Phe His Gly Ile
             20                  25                  30

Lys Gln Ala Leu Asn Glu Cys Gly Ala Ser Val Phe Val Pro Ile Ile
         35                  40                  45

Ser Ala Ala Asn Asp Asn Glu Ala Arg Gly Asp Gln Leu Leu Lys Gln
     50                  55                  60

Ile His Asn Leu Arg Arg Gln Val Gly Ala Gln Arg Val Asn Leu Ile
 65                  70                  75                  80

Gly His Ser Gln Gly Ala Leu Thr Ala Arg Tyr Val Ala Ala Ile Ala
                 85                  90                  95

Pro Glu Leu Ile Ala Ser Val Thr Ser Val Ser Gly Pro Asn His Gly
             100                 105                 110

Ser Glu Leu Ala Asp Arg Leu Arg Leu Ala Phe Val Pro Gly Arg Leu
         115                 120                 125

Gly Glu Thr Val Ala Ala Ala Leu Thr Thr Ser Phe Ser Ala Phe Leu
     130                 135                 140

Ser Ala Leu Ser Gly His Pro Arg Leu Pro Gln Asn Ala Leu Asn Ala
145                 150                 155                 160

Leu Asn Ala Leu Thr Thr Asp Gly Val Ala Ala Phe Asn Arg Gln Tyr
                 165                 170                 175

Pro Gln Gly Leu Pro Asp Arg Trp Gly Gly Met Gly Pro Ala Gln Val
             180                 185                 190

Asn Ala Val His Tyr Tyr Ser Trp Ser Gly Ile Ile Lys Gly Ser Arg
         195                 200                 205

Leu Ala Glu Ser Leu Asn Leu Leu Asp Pro Leu His Asn Ala Leu Arg
     210                 215                 220

Val Phe Asp Ser Phe Phe Thr Arg Glu Thr Arg Glu Asn Asp Gly Met
225                 230                 235                 240

Val Gly Arg Phe Ser Ser His Leu Gly Gln Val Ile Arg Ser Asp Tyr
                 245                 250                 255

Pro Leu Asp His Leu Asp Thr Ile Asn His Met Ala Arg Gly Ser Ala
             260                 265                 270

Gly Ala Ser Thr Arg
             275
```

(2) INFORMATION FOR SEQ ID NO: 4:

(i) SEQUENCE CHARACTERISTICS:
      (A) LENGTH: 269 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 4:

```
Ser Ile Asp Gly Gly Ile Arg Ala Ala Thr Ser Gln Glu Ile Asn Glu
 1               5                  10                  15

Leu Thr Tyr Tyr Thr Thr Leu Ser Ala Asn Ser Tyr Cys Arg Thr Val
             20                  25                  30

Ile Pro Gly Ala Thr Trp Asp Cys Ile His Cys Asp Ala Thr Glu Asp
         35                  40                  45

Leu Lys Ile Ile Lys Thr Trp Ser Thr Leu Ile Tyr Asp Thr Asn Ala
     50                  55                  60
```

```
Met Val Ala Arg Gly Asp Ser Glu Lys Thr Ile Tyr Ile Val Phe Arg
 65                  70                  75                  80

Gly Ser Ser Ser Ile Arg Asn Trp Ile Ala Asp Leu Thr Phe Val Pro
                 85                  90                  95

Val Ser Tyr Pro Pro Val Ser Gly Thr Lys Val His Lys Gly Phe Leu
            100                 105                 110

Asp Ser Tyr Gly Glu Val Gln Asn Glu Leu Val Ala Thr Val Leu Asp
        115                 120                 125

Gln Phe Lys Gln Tyr Pro Ser Tyr Lys Val Ala Val Thr Gly His Ser
130                 135                 140

Leu Gly Gly Ala Thr Ala Leu Leu Cys Ala Leu Gly Leu Tyr Gln Arg
145                 150                 155                 160

Glu Glu Gly Leu Ser Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
210                 215                 220

Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Ser
            260                 265
```

(2) INFORMATION FOR SEQ ID NO: 5:

(i) SEQUENCE CHARACTERISTICS:
        (A) LENGTH: 297 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

```
Asp Asp Asn Leu Val Gly Gly Met Thr Leu Asp Leu Pro Ser Asp Ala
1               5                   10                  15

Pro Pro Ile Ser Leu Ser Ser Thr Asn Ser Ala Ser Asp Gly Gly
                 20                  25                  30

Lys Val Val Ala Ala Thr Thr Ala Gln Ile Gln Glu Phe Thr Lys Tyr
             35                  40                  45

Ala Gly Ile Ala Ala Thr Ala Tyr Cys Arg Ser Val Val Pro Gly Asn
         50                  55                  60

Lys Trp Asp Cys Val Gln Cys Gln Lys Trp Val Pro Asp Gly Lys Ile
 65                  70                  75                  80

Ile Thr Thr Phe Thr Ser Leu Leu Ser Asp Thr Asn Gly Tyr Val Leu
                 85                  90                  95

Arg Ser Asp Lys Gln Lys Thr Ile Tyr Leu Val Phe Arg Gly Thr Asn
            100                 105                 110

Ser Phe Arg Ser Ala Ile Thr Asp Ile Val Phe Asn Phe Ser Asp Tyr
        115                 120                 125

Lys Pro Val Lys Gly Ala Lys Val His Ala Gly Phe Leu Ser Ser Tyr
130                 135                 140
```

```
Glu Gln Val Val Asn Asp Tyr Phe Pro Val Val Gln Glu Gln Leu Thr
145                 150                 155                 160

Ala His Pro Thr Tyr Lys Val Ile Val Thr Gly His Ser Leu Gly Gly
                165                 170                 175

Ala Gln Ala Leu Leu Ala Gly Met Asp Leu Tyr Gln Arg Glu Pro Arg
            180                 185                 190

Leu Ser Pro Lys Asn Leu Ser Ile Phe Thr Val Gly Gly Pro Arg Val
        195                 200                 205

Gly Asn Pro Thr Phe Ala Tyr Tyr Val Glu Ser Thr Gly Ile Pro Phe
    210                 215                 220

Gln Arg Thr Val His Lys Arg Asp Ile Val Pro His Val Pro Pro Gln
225                 230                 235                 240

Ser Phe Gly Phe Leu His Pro Gly Val Glu Ser Trp Ile Lys Ser Gly
                245                 250                 255

Thr Ser Asn Val Gln Ile Cys Thr Ser Glu Ile Glu Thr Lys Asp Cys
            260                 265                 270

Ser Asn Ser Ile Val Pro Phe Thr Ser Ile Leu Asp His Leu Ser Tyr
        275                 280                 285

Phe Asp Ile Asn Glu Gly Ser Cys Leu
    290                 295
```

(2) INFORMATION FOR SEQ ID NO: 6:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
GCTGCTCTGC CTAACCCTTA CGACGACCCT TTCTACACCA CCCC                44
```

(2) INFORMATION FOR SEQ ID NO: 7:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
TTCTTGAGCG CGCGGATGCC GTCGAGGATA GCCATGCCCT CTTCGTAGCC AGCGATCCAG    60

GCGGCTTTGA AGCCTTCGTG                                                80
```

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
CAGAACGAGG CGGTGGCCGA C                                          21
```

(2) INFORMATION FOR SEQ ID NO: 9:

```
    (i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

TTCTTGAGCG CGCGGATGCC GTCGAGGATA GCCATGCCCT CTTCGTAGCC AGCGATGAAG        60

GCGGCTTTCC AGCCTTCGTG                                                   80

(2) INFORMATION FOR SEQ ID NO: 10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

AACCCATACG ACGACCC                                                      17

(2) INFORMATION FOR SEQ ID NO: 11:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

TTCTTGAGCG CGCGGATGCC GTCGAGGATA GCCATGCCCT CTTCGTAGCC AGCGATCCAG        60

GCGGCTTTCC AGCCTTCGTG                                                   80
```

C. ANTARCTICA LIPASE VARIANTS

CROSS-REFERENCE TO RELATED APPLICATIONS

This application is a PCT/DK93/00225 filed Jul. 5, 1993, which is incorporated herein by reference.

FIELD OF THE INVENTION

The present invention relates to novel lipase enzyme variants with improved properties, DNA constructs coding for the expression of said variants, host cells capable of expressing the variants from the DNA constructs, as well as a method of producing the variants by cultivation of said host cells. Furthermore, the present invention relates to a recombinant essentially pure *Candida antarctica* lipase and variants thereof as well as a DNA sequence encoding the said lipase or variants thereof.

BACKGROUND OF THE INVENTION

A wide variety of lipases of microbial and mammalian origin are known. The amino acid sequence of many of these lipases have been elucidated and analyzed with respect to structural and functional elements important for their catalytic function, see, for instance, Winkler et al., 1990 and Schrag et al., 1991. It has been found that the lipase enzyme upon binding of a lipid substrate and activation undergoes a conformational change, which inter alia, results in an exposure of the active site to the substrate. This conformational change together with the presumed interaction between enzyme and substrate have been discussed by, inter alia, Brady et al., 1990, Brzozowski et al., 1991, Derewenda et al., 1992.

Based on the knowledge of the structure of a number of lipases, it has been possible to construct lipase variants having improved properties by use of recombinant DNA techniques. Thus, WO 92/05249 discloses the construction of certain lipase variants, in which the lipid contact zone has been modified so as to provide the variants with different substrate specificities and/or an improved accessibility of the active site of the lipase to a lipid substrate. The modifications involve changing the electrostatic charge, hydrophobicity or the surface conformation of the lipid contact zone by way of amino acid substitutions.

Although the structural and functional relationship of lipases have been the subject of a number of studies as described in the above cited references, the research has mainly focused on the macroscopic characteristics of the lipases upon substrate binding and activation, whereas the identity of the amino acids actually involved in the substrate binding and catalytic activity has been discussed only to a lesser extent.

SUMMARY OF THE INVENTION

By sequence alignment analysis combined with analysis of the structure and activity of a number of lipases, the present inventors have now surprisingly found that the presence of certain amino acids, especially tryptophan, in a critical position of the lipase seems to be important for optimal catalytic activity.

It is consequently an object of the present invention to modify lipases which do not comprise such an amino acid residue in the critical position (which lipases in the present context are termed parent lipases) by replacing the amino acid residue located in this position with an amino acid residue which gives rise to a variant having an increased specific activity.

More specifically, in one aspect the present invention relates to a lipase variant of a parent lipase comprising a trypsin-like catalytic triad including an active serine located in a predominantly hydrophobic, elongated binding pocket of the lipase molecule and, located in a critical position of a lipid contact zone of the lipase structure, an amino acid residue different from an aromatic amino acid residue, which interacts with a lipid substrate at or during hydrolysis, in which lipase variant said amino acid residue has been replaced by an aromatic amino acid residue so as to confer to the variant an increased specific activity as compared to that of the parent lipase.

In the present context, the term "trypsin-like" is intended to indicate that the parent lipase comprises a catalytic triad at the active site corresponding to that of trypsin, i.e. the amino acids Ser, His and one of Asp, Glu, Asn or Gln.

Lipases degrade triglycerides down to fatty acids, glycerol and di- and/or monoglycerides. The lipase action depends on interfacial activation of the lipase in the presence of substrate surfaces. On activation lipases change their conformation in such a manner that their surface hydrophobicity in an area around the active site is increased. The interfacial activation of lipases is discussed by Tilbeurgh et al. (1993).

All lipases studied until now have been found to comprise at least one surface loop structure (also termed a lid or a flap) which covers the active serine when the lipase is in inactive form (an example of such a lipase is described by Brady et al., 1990). When the lipase is activated, the loop structure is shifted to expose the active site residues, creating a surface surrounding the active site Ser, which has an increased surface hydrophobicity and which interacts with the lipid substrate at or during hydrolysis. For the present purpose, this surface is termed the "lipid contact zone", intended to include amino acid residues located within or forming part of this surface, optionally in the form of loop structures. These residues may participate in lipase interaction with the substrate at or during hydrolysis where the lipase hydrolyses triglycerides from the lipid phase when activated by contact with the lipid surface.

The lipid contact zone contains a binding area (a so-called binding pocket) for the lipid substrate which is the part of the lipid contact zone to which the lipid substrate binds before hydrolysis. This binding area again contains a so-called hydrolysis pocket, which is situated around the active site Ser, and in which the hydrolysis of the lipid substrate is believed to take place. In all known lipases to date the lipid contact zone is easily recognized, e.g. from a three-dimensional structure of the lipase created by suitable computer programs. The conformation of an inactive and activated lipase, respectively, is shown in FIG. 1 which is further discussed below.

In the present context, the "critical position" of the lipase molecule is the position in the lipid contact zone of the lipase molecule, which is occupied by an amino acid residue which interacts with the lipid substrate and which is different from an aromatic amino acid residue.

In another aspect the present invention relates an *C. antarctica* lipase A which is essentially free from other *C. antarctica* substances and which comprises the amino acid sequence identified in SEQ ID No. 2 or a variant thereof which 1) has lipase activity, 2) reacts with an antibody reactive with at least one epitope of the *C. antarctica* lipase having the amino acid sequence shown in SEQ ID No. 2, and/or 3) is encoded by a nucleotide sequence which hybridizes with an oligonucleotide probe prepared on the basis of the full or partial nucleotide sequence shown in SEQ ID No. 1 encoding the *C. antarctica* lipase A.

The *C. antarctica* lipase A of the invention has a number of desirable properties including a high thermostability and activity at acidic pH and may advantageously be produced by use of recombinant DNA techniques, e.g. using the procedures described below. Thus, the lipase A of the invention may be obtained in a higher purity and a higher amount than the *C. antarctica* lipase A purified from wild type *C. antarctica* which is described in WO 88/02775.

Furthermore, the present invention relates to a DNA sequence encoding the *C. antarctica* lipase A having the amino acid sequence identified in SEQ ID No. 2 or a modification of said DNA sequence encoding a variant of the *C. antarctica* lipase A as defined above.

In the present context "*C. antarctica* lipase A" is used inter-changeably with "lipase A" and the variant of the *C. antarctica* lipase A is termed "lipase A variant".

The present invention also relates to a DNA construct comprising a DNA sequence encoding a lipase variant as indicated above or a DNA sequence encoding the *C. antarctica* lipase A, a recombinant expression vector carrying said DNA construct, a cell transformed with the DNA construct or the expression vector, as well as a method of producing a lipase variant of the invention by culturing said cell under conditions conducive to the production of the lipase variant, after which the lipase variant is recovered from the culture.

It will be understood that lipase variants of the present invention having an increased specific activity as compared to their parent lipases may be used for the same purposes as their parent lipases, advantageously in a lower amount due to their higher specific activity.

Accordingly, the present invention relates to the use of a lipase variant of the invention as a detergent enzyme; as a digestive enzyme; in ester hydrolysis, ester synthesis or interesterification; or the use of the lipase variant to avoid pitch trouble arising, e.g., in processes for preparing mechanical pulp and in paper-making processes using mechanical pulp.

DETAILED DISCLOSURE OF THE INVENTION

As indicated above, the present inventors have found that the presence of certain aromatic amino acids, especially tryptophan, located in the lipid contact zone of the lipase molecule is important for optimal catalytic activity.

The importance of the presence of an aromatic amino acid residue and in particular a tryptophan residue was found in connection with a study of mutants of a *Humicola lanuginosa* lipase which comprises a tryptophan residue at the critical position in the lipid contact zone, i.e. the amino acid number in the amino acid sequence of the *H. lanucinosa* lipase published in EP 0 305 216. In the *H. lanuginosa* mutants this is tryptophan residue was replaced by phenylalanine, tyrosine, histidine, isoleucine, glutamic acid and glycine, respectively. It was found that the specific activity of these mutants decreased (in the order indicated above) from 100% of the wild type lipase to about 10% for the phenylalanine mutant and down to about 2% for the glycine mutant.

Without being limited to any theory it is presently believed that the amino acid residue present in the critical position, e.g. on top of or in the proximity of the active serine, may be involved in a) stabilization of the tetrahedral intermediate formed from the lipase and the substrate during the activation of the lipase, and b) in the activation of the replacement of the lid region covering the active serine in the inactive enzyme. When tryptophan is present in this position, it is contemplated that optimal performance with respect to a) as well as b) above is obtained. Thus, it is believed that tryptophan gives rise to the formation of the most stable tetrahedral intermediate (which means a lowering of the activation energy needed for the catalysis to take place), and further improves the performance of the enzyme with respect to the activation of the lid opening which is essential for any catalysis to take place.

In connection with a) above it has been observed that the best acting lipase variants contain an unsaturated ring system in the side-chain. The biggest unsaturated system is tryptophan, then tyrosine, phenylalanine and histidine. These sidechains have a pi-electron system ("the unsaturation") that could be important for the proton transfer in the catalysis resulting in a lower activation energy for creating the tetrahedral intermediate where proton transfer has taken place from active site histidine to serine to the oxyanion hole created after lid activation and opening.

From the above theoretical explanation it will be understood that the optimal amino acid to be present in the critical position, e.g. on top of or in the proximity of the active serine, is tryptophan. However, when the parent lipase is one which does not contain any aromatic amino acid residue or any amino acid residue with an unsaturated ring system in the side-chain in this position, such amino acids may advantageously be substituted into this position.

Thus, when the parent lipase, in the critical position, has an amino acid residue which does not comprise an unsaturated ring system in the side-chain, an amino acid residue having such an unsaturated ring-system, e.g. an aromatic amino acid (tryptophan, tyrosine, phenylalanine or histidine) may be substituted into the critical position. When the amino acid residue in the critical position of the parent lipase is histidine, it may advantageously be replaced by phenylalanine, tyrosine and most preferably tryptophan, when the amino acid residue is tyrosine, it may advantageously be replaced by phenylalanine and most preferably tryptophan, and when the amino acid residue is phenylalanine it may advantageously be replaced by tryptophan.

While the critical position in some lipases is contemplated to be any position within the lipid contact zone, the critical position will normally be located in the binding pocket of the lipase molecule, and preferably in the hydrolysis pocket thereof. For most lipases it is believed that the critical amino acid residue is positioned on top of or in the proximity of the active site.

The amino acid residue occupying this position may be identified in any lipase by 1) sequence alignment studies in which the amino acid sequence of the lipase in question is aligned with the amino acid sequence of other lipases, in which the amino acid residue positioned on top of or in the proximity of the active serine has been identified, so as to identify the presumed position of said amino acid residue, and/or 2) an analysis of the three-dimensional structure of the lipase in question using standard display programmes such as INSIGHT (Biosym Technologies Inc., San Diego, USA), so as to identify the amino acid sequence on top of or in the proximity of the active serine.

More specifically, on the basis of a computer program such as INSIGHT displaying lipase coordinates in accordance with well-known technology, it is simple to point out which part of the lipase contains the lipid contact zone. 1/ if the structure of the lipase is in a non-activated form, the lipid contact zone is identified by the direction of sidechains of the active site Ser. 2/ if the structure is in the activated form one may additionally base the identification on a colouring of all hydrophobic residues in a colour different from the other residues. By this procedure in which a Corey, Pauling, Koltun model of the structure is created, the hydrophobic surface specific for the lipid contact zone may be identified. The active site Ser is located within this more hydrophobic part of the molecule.

In some lipases the critical amino acid residue is located in the surface loop structure covering the active site, or in one or more of the surface loop structures found to form part of the surface of the lipid contact zone, such as of the binding pocket or hydrolysis pocket.

Although the critical position is normally considered to be constituted of only one amino acid residue it may be advantageous to replace two or more residues, preferably with a tryptophan residue as explained above, in order to obtain a further increased specific activity.

It is contemplated that it is possible to increase the specific activity of parent lipases which do not have a tryptophan residue in the critical position at least 2 times, such as at least 3 and preferably at least 4 or even 5, 6 or 7 times by modifications as diclosed herein.

It is contemplated that lipase variants as defined herein having an increased substrate specificity may be prepared on the basis of parent lipases of various origins. Thus, the parent lipase may be a microbial lipase or a mammalian lipase.

When the parent lipase is a microbial lipase, it may be selected from yeast, e.g. Candida, lipases, bacterial, e.g. Pseudomonas, lipases or fungal, e.g. Humicola or Rhizomucor lipases.

One preferred lipase variant is one, in which the parent lipase is derived from a strain of *Candida antarctica*, in particular one in which the parent lipase is lipase A of *C. antarctica*, preferably the one which has the amino acid sequence shown in SEQ ID No. 2 or a lipase A variant thereof as defined herein. The lipase variant of this *C. antarctica* lipase A preferably has the amino acid sequence shown in SEQ ID No. 2 in which the phenylalanine 139 of the parent lipase has been replaced by a tryptophan residue. The construction of this variant and the analysis of the properties thereof is discussed in Example 3, 5 and 6.

A lipase variant of the invention may, as mentioned above, be prepared on the basis of a parent lipase derived from a strain of a Pseudomonas species, e.g. Ps. fragi. An example of a suitable Ps. frapi lipase which has an amino acid residue different from tryptophan positioned on top of or in the proximity of the active serine, is the one described by Aoyama et al., 1988. A lipase variant according to the present invention may be constructed by replacing the phenylalanine residue 29 in the amino acid sequence of said lipase shown in SEQ ID No. 3 by a tryptophan residue.

An example of a fungal lipase suitable as a parent lipase for the construction of a lipase variant of the invention is one derived from Rhizopus, especially from *R. delemar* or *R. niveus*, the amino acid sequence of which latter is disclosed in, e.g., JP 64-80290. In order to construct a lipase variant according to the present invention from this parent lipase, the alanine residue at position 117 is to be replaced with an aromatic amino acid residue such as tryptophan. The sequence alignment of the *R. niveus* lipase sequence (SEQ ID No. 5) and an *Rhizomucor miehei* lipase sequence (containing a tryptophan residue) (SEQ ID No. 4) is illustrated below. From this alignment the critical position of the *R. niveus* lipase may be determined.

```
SEQUENCE            10        20        30        40        50        60      Res# mucor     --------------------------SIDGGIRAATSQEINELTYYTTLSANSYCRTV         32
niveus    DDNLVGGMTLDLPSDAPPISLSSSTNSASDGGKVVAATTAQIQEFTKYAGIAATAYCRSV        60

SEQUENCE            70        80        90       100       110       120      Res# mucor     IPGATWDCIHCDATE-DLKIIKTWSTLIYDTNAMVARGDSEKTIYIVFRGSSSIRNWIAD        91
niveus    VPGNKWDCVQCQKWVPDGKIITTFTSLLSDTNGYVLRSDKQKTTYLVFRGINSFRSAITD       120

SEQUENCE           130       140       150       160       170       180      Res# mucor     LTFVPVSYPPVSGTKVHKGFLDSYGEVQNELVATVLDQFKQYPSYKVAVTGHSLGGATAL       151
niveus    IVFNFSDYKPVKGAKVHAGFLSSYEQVVNDYFPVVQEQLTAHPTYKVIVTGHSLGGAQAL       180

SEQUENCE           190       200       210       220       230       240      Res# mucor     LCALGLYQREEGLSSSNLFLYTQGQPRVGDPAFANYVVSTGIPYRRTVNERDIVPHLPPA       211
niveus    LAGMDLYQREPRLSPKNLSIFTVGGPRVGNPTFAYYVESTGIPFQRTVHKRDIVPHVPPQ       240

SEQUENCE           250       260       270       280       290       300      Res# mucor     AFGFLHAGEEYWITDNSPETVQVCTSDLETSDCSNSIVPFTSVLDHLSYFGINTGLCS         269
niveus    SFGFLHPGVESWIKSGTSN-VQICTSETETKDCSNSIVPFTSILDHLSYFDINEGSCL        297
```

The present inventors have surprisingly found that non-pancreatic lipases such as gastric, lingual, or hepatic lipases have the common feature that the amino acid residue which has been identified to be the one located in the critical position of the lipase molecule, normally on top of or in the proximity of the active serine, is different from tryptophan. This is in contrast to pancreatic lipases which generally have been found to have a tryptophan residue in this position. Thus, in the present context, non-pancreatic mammalian lipases may advantageously be used as "parent lipases" for the construction of lipase variants of the invention.

Accordingly, lipase variants as disclosed herein which is of mammalian origin is advantageously prepared from a parent lipase of non-pancreatic, such as gastric, lingual or hepatic origin. Such mammalian lipases may be derived from humans, rats, mice, pigs, dogs or other mammals. Specific examples of such mammalian lipases includes a rat lingual lipase having the sequence identified as A23045 (Docherty et al., 1985), a rat hepatic lipase having the sequence identified as A27442 (Komaromy and Schotz, 1987), a human hepatic lipase having the sequence identified as A33553 (Datta et al., 1988), a human gastric lipase having the sequence identified as S07145 (Bodmer et al., 1987), and a Bio Salt Activated Lipase (BSAL) having the sequence identified as A37916 (Baba et al., 1991) all of which were analysed with respect to the critical position in the sequence alignment analysis illustrated below. The pancreatic lipases included in this sequence alignment study were a murine pancreatic lipase, A34671 (Grusby et al., 1990), a porcine pancreatic lipase, A00732 (Caro et al., 1981), a human pancreatic lipase, A34494 (Lowe et al., 1989), and a canine pancreatic lipase having the sequence B24392 (Mickel et al., 1989). The amino acid sequences of each of the lipases mentioned have the accession numbers listed above and are available from publically available databases.

```
            42                                                      89
A37916  TYGEDCLYL   NIWVPQGRK.  ..QVSRDLPV  MIWIYGGAFL  MGSGHGANFL
A23045  EVVTEDGYIL  GVYRIPHGKN  NSENIGKRPV  VYLQHGLIAS  AT..NWIANL
S07145  EVVTEDGYIL  EVNRIPYGKK  NSGNTGQRPV  VFLQHGLLAS  AT..NWISNL
B24392  TNKNPNNFQT  LLPSDPSTIE  ASNFQTDKKT  RFTIHGFINK  GE.ENWLLDM
A34494  TNENPNNFQE  VA.ADSSSIS  GSNFKTNRKT  RFIIHGFIDK  GE.ENWLANV
A34671  TNENPNNYQI  ISATDATIN   ASNFQLDRKT  RFIIHGFIDK  BE.EGWLLDM
A00732  TNQNQNNYQE  LV.ADPSTIT  NSNFRMDRKT  RFIIHGFIDK  GE.EDWLSNI
A33553  GETNQ..GCQ  IRINHPDTLQ  ECGFNSSLPL  VMIIHGWSVD  GVLENWIWQM
A27442  KDESDRLGCQ  LRPQHPETLQ  ECGFNSSHPL  VMIIHGWSVD  GLLETWIWKI 90                                                      130
A37916  NNYLYDGEEI  ATRGNVIVVT  FNYRVGPLGF  LSTGDANLPG  NYGLRDQHMA
A23045  PNNSLAFMIA  DAGYDVWLGN  SRGNTWSRKN  VYYSPDSVEF  WAFSFDEMAK
S07145  PNNSLAFILA  DAGYDVWLGN  SRGNTWARRN  LYYSPDSVEF  WAFSFDEMAK
B24392  CKNMFKVEE.  ........VN  CICVDWKKGS  QTSYTQAANN  VRVVGAQVAQ
A34494  CKNLFKVES.  ........VN  CICVDWKGGS  RTGYTQASQN  IRIVGAEVAY
A34671  CKKMFQVEK.  ........VN  CICVDWKRGS  RTEYTQASYN  TRVVGAEIAF
A00732  CKNLFKVES.  ........VN  CICVDWKGGS  RTGYTQASQN  IRIVGAEVAY
A33553  VAALKSQPAQ  P.......VN  VGLVDWITLA  HDHYTIAVRN  TRLVGKEVAA
A27442  VGALKSRQSQ  P.......VN  VGLVDWISLA  YQHYAIAVRN  TRVVGQEVAA

131                              ┌──────────┐            175
A37916  IAWVKRNI.A  AFGGDPNNTT  │LFGESAGGAS│ VSLQTLSPYN  K...GLIRRA
A23045  YDLPATINFI  VQKTGQEKIH  │YVGHSQGTTI│ GFIAFSTINPT L..AKKIKTF
S07145  YDLPATIDFI  VKKTGQKQLH  │YVGHSQGTTI│ GFIAFSTINPS L..AKRIKTF
B24392  MLSMLS...A  NYSYSPSQVQ  │LIGHSLGAHV│ AGEAGSRTPG  ...LGROTGL
A34494  FVEFLQ...S  AFGYSPSNVH  │VIGHSLGAHA│ AGEAGRRTNG  T..IGRITGL
A34671  LVQVLS...T  EMGYSPENVH  │LIGHSKGSHV│ AGEAGRRLEG  H..VGRITGL
A00732  FVEVLK...S  SLGYSPSNVH  │VIGHSLGSHA│ AGEAGRRTNG  T..IERITGL
A33553  LLRWLE...E  SVQLSRSHVH  │LIGYSLGAHV│ SGFAGSSIGG  THKIGRITGL
A27442  LLLWLE...E  SMKFSRSKVH  │LIGYSLGAHV│ SGFAGSSMGG  KRKIGRITGL
                                 └──────────┘

176                                                     220
A37916  ISQSGVALSP  WVIQKN....  ..PLFWAKKV  AEKVGCPVGD  AARMAQCLKV
A23045  YALAPVATVK  YTQSPLKKIS  FIPTFLFKLM  FGKKMFLPHT  YFDDFLGTEV
S07145  YALAPVATVK  YTKSLINKLR  FVPQSLFKFI  FGDKIFYPHN  FFDQFLATEV
B24392  DPVEASFQGT  PEEVRLD...  ..PTDADFVD  VIHTDGAPIV  PFLGFGTSQQ
A34494  DPAEPCFQGT  PELVRLD...  ..PSDAKFVD  VIHTDGAPIV  PNLGFGMSQV
A34671  DPAEPCFQGL  PEEVRLD...  ..PSDAMFVD  VIHTDAAPII  PYLGFGMSQK
A00732  DPAEPCFQGT  PELVRLD...  ..PSDAKFVD  VIHTDAAPII  PNLGFGMSQT
A33553  DAAGPLFEGS  APSNRLS...  ..PDDASFVD  AIHTFTREHM  GLSVGIK.QP
A27442  DPAGPMFEGT  SPNERLS...  ..PDDANFVD  AIHTFTREHM  GLSVGIK.QP
```

-continued

|  | 221 | | Z = Flap region | | 270 |
|---|---|---|---|---|---|
| A37916 | TDPRALTLAY | KVPLAGLEYP | MLHYVGFVPV | IDGDFIPADP | INLYANAADI |
| A23045 | CSREVLDLLC | SNTLFIFCGF | DKKNLNVSRF | DVYLGHNPAG | TSVQDFLHWA |
| S07145 | CSREMLNLLC | SNALFIICGF | DSKNFNTSRL | DVYLSHNPAG | TSVQNMFHWT |
| B24392 | MGHLDFFPNG | GEEMPGCKKN | ALSQIVNLDG | IWEGTRDFVA | CNHLRSYKYY |
| A34494 | VGHLDFFPNG | GVEMPGCKKN | ILSQIVDIDG | IWEGTRDFAA | CNHLRSYKYY |
| A34671 | VGHLDFFPNG | GKEIPGCQKN | ILSTIVDING | IWEGTRNFAA | CNHLRSYKYY |
| A00732 | VGHLDFFPNG | GKQMPGCQKN | ILSQIVDIDG | IWEGTRDFVA | CNHLRSYKYY |
| A33553 | IGHYDFYPNG | GSFQPGCHFL | ELYRHIAQHG | FNAITQTIK. | CSHERSVHLF |
| A27442 | IAHYDFYPNG | GSFQPGCHFL | ELYKHIAEHG | LNAITQTIK. | CAHERSVHLF |

As mentioned above the present invention also relates to a C. antarctica lipase A essentially free from other C. antarctica substances, which has the amino acid sequence shown in SEQ ID No. 2 or a variant therof which 1) has lipase activity, 2) reacts with an antibody reactive with at least one epitope of C. antarctica lipase A having the amino acid sequence shown in SEQ ID No. 2, and/or 3) is encoded by a nucleotide sequence which hybridizes with an oligonucleotide probe prepared on the basis of the full or partial nucleotide sequence shown in SEQ ID No. 1 encoding the C. antarctica lipase A.

In the present context, the term "variant" is intended to indicate a lipase A variant which is derived from the C. antarctica lipase A having the amino acid sequence shown in SEQ ID No. 2, or a naturally occurring variant. Typically, the variant differ from the native lipase A by one or more amino acid residues, which may have been added or deleted from either or both of the N-terminal or C-terminal end of the lipase, inserted or deleted at one or more sites within the amino acid sequence of the lipase or substituted with one or more amino acid residues within, or at either or both ends of the amino acid sequence of the lipase.

Furthermore, the variant of the invention has one or more of the characterizing properties 1)-3) mentioned above. Property 1), i.e. the "lipase activity" of the variant may be determined using any known lipase assay, e.g. the Standard LU assay described in the Methods section below.

Property 2), i.e. the reactivity of the variant of the invention with an antibody raised against or reactive with at least one epitope of the C. antarctica lipase A having the amino acid sequence shown in SEQ ID No. 2 below may be determined by polyclonal antibodies produced in a known manner, for instance by immunization of a rabbit with the C. antarctica lipase A of the invention. The antibody reactivity may be determined using assays known in the art, examples of which are Western Blotting or radial immunodiffusion assay.

Property 3) above, involving hybridization, may be performed using an oligonucleotide probe prepared on the basis of the full or partial cDNA sequence encoding the C. antarctica lipase A, the amino acid sequence of which is identified in SEQ ID No. 2, as a hybridization probe in a hybridization experiment carried out under standard hybridization conditions. For instance, such conditions are hybridization under specified conditions, e.g. involving presoaking in 5×SSC and prehybridizing for 1 h at ~40° C. in a solution of 20% formamide, 5×Denhardt's solution, 50 mM sodium phosphate, pH 6.8, and 50 µg of denatured sonicated calf thymus DNA, followed by hybridization in the same solution supplemented with 100 µM ATP for 18 h at ~40° C., or other methods described by e.g. Sambrook et al., 1989.

The nucleotide sequence on the basis of which the oligonucleotide probe is prepared is conveniently the DNA sequence shown in SEQ ID No. 1.

As stated above in a further aspect the present invention relates to a DNA sequence encoding C. antarctica lipase A having the amino acid sequence shown in SEQ ID No. 2 or a modification of said DNA sequence which encodes a variant of C. antarctica lipase A which 1) has lipase activity, 2) reacts with an antibody reactive with at least one epitope of the C. antarctica lipase A having the amino acid sequence shown in SEQ ID No. 2, and/or 3) is encoded by a nucleotide sequence which hybridizes with an oligonucleotide probe prepared on the basis of the full or partial nucleotide sequence shown in SEQ ID No. 1 encoding the C. antarctica lipase A.

Examples of suitable modifications of the DNA sequence are nucleotide substitutions which do not give rise to another amino acid sequence of the encoded enzyme, but which may correspond to the codon usage of the host organism into which the DNA sequence is introduced or nucleotide substitutions which do give rise to a different amino acid sequence, without, however, impairing the above stated properties of the enzyme. Other examples of possible modifications are insertion of one or more nucleotides into the sequence, addition of one or more nucleotides at either end of the sequence and deletion of one or more nucleotides at either end of or within the sequence.

Methods of Preparing Lipase Variants of the Invention

Several methods for introducing mutations into genes are known in the art. After a brief discussion of cloning lipase-encoding DNA sequences, methods for generating mutations at specific sites within the lipase-encoding sequence will be discussed.

Cloning a DNA Sequence Encoding a Lipase

The DNA sequence encoding a parent lipase or the C. antarctica lipase A as defined herein may be isolated from any cell or microorganism producing the lipase in question by various methods, well known in the art. First a genomic DNA and/or cDNA library should be constructed using chromosomal DNA or messenger RNA from the organism that produces the lipase to be studied. Then, if the amino acid sequence of the lipase is known, homologous, labelled oligonucleotide probes may be synthesized and used to identify lipase-encoding clones from a genomic library of bacterial DNA, or from a fungal cDNA library. Alternatively, a labelled oligonucleotide probe containing sequences homologous to lipase from another strain of bacteria or fungus could be used as a probe to identify lipase-encoding clones, using hybridization and washing conditions of lower stringency.

Yet another method for identifying lipase-producing clones would involve inserting fragments of genomic DNA into an expression vector, such as a plasmid, transforming lipase-negative bacteria with the resulting genomic DNA library, and then plating the transformed bacteria onto agar containing a substrate for lipase. Those bacteria containing lipase-bearing plasmid will produce colonies surrounded by a halo of clear agar, due to digestion of the substrate by secreted lipase.

Alternatively, the DNA sequence encoding the enzyme may be prepared synthetically by established standard methods, e.g. the phosphoamidite method described by S. L. Beaucage and M. H. Caruthers (1981) or the method described by Matthes et al. (1984). According to the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence, in accordance with standard techniques. The DNA sequence may also be prepared by polymerase chain reaction (PCR) using specific primers, for instance as described in U.S. Pat. No. 4,683,202 or R. K. Saiki et al. (1988).

Site-Directed Mutagenesis of the Lipase-Encoding Sequence

Once a lipase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the lipase-encoding sequence, is created in a vector carrying the lipase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette, however, an even greater variety of mutations can be introduced at any one time by the Morinaga method, because a multitude of oligonucleotides, of various lengths, can be introduced.

Another method of introducing mutations into lipase-encoding sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Expression of Lipase Variants

According to the invention, a *C. antarctica* lipase A-coding sequence or a mutated lipase-coding sequence produced by methods described above or any alternative methods known in the art, can be expressed, in enzyme form, using an expression vector which typically includes control sequences encoding a promoter, operator, ribosome binding site, translation initiation signal, and, optionally, a repressor gene or various activator genes. To permit the secretion of the expressed protein, nucleotides encoding a "signal sequence" may be inserted prior to the lipase-coding sequence. For expression under the direction of control sequences, a target gene to be treated according to the invention is operably linked to the control sequences in the proper reading frame. Promoter sequences that can be incorporated into plasmid vectors, and which can support the transcription of the mutant lipase gene, include but are not limited to the prokaryotic β-lactamase promoter (Villa-Kamaroff et al. (1978) and the tac promoter (DeBoer, et al., 1983). Further references can also be found in "Useful proteins from recombinant bacteria" (1980).

According to one embodiment a strain of Bacillus, e.g. *B. subtilis, B. licheniformis* or *B. lentus*, or a strain of *E. coli* is transformed by an expression vector carrying the lipase A or the mutated DNA. If expression is to take place in a secreting microorganism such as *B. subtilis* a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when is present.

The lipase or lipase variants of the invention may further be produced by using a yeast cell has a host cell. Examples of suitable yeast host cells include a strain of Saccharomyces, such as *S. cerevisiae,* or a strain of Hansenula, e.g. *H. polymorpha* or Pichia, e.g. *P. pastoris.*

In a currently preferred method of producing lipase A or lipase variants of the invention, a filamentous fungus is used as the host organism. The filamentous fungus host organism may conveniently be one which has previously been used as a host for producing recombinant proteins, e.g. a strain of Aspergillus sp., such as *A. niger, A. nidulans* or *A. oryzae.* The use of *A. oryzae* in the production of recombinant proteins is extensively described in, e.g. EP 238 023.

For expression of lipase variants in Aspergillus, the DNA sequence coding for the lipase A or the lipase variant is preceded by a promoter. The promoter may be any DNA sequence exhibiting a strong transcriptional activity in Aspergillus and may be derived from a gene encoding an extracellular or intracellular protein such as an amylase, a glucoamylase, a protease, a lipase, a cellulase or a glycolytic enzyme.

Examples of suitable promoters are those derived from the genes encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease or *A. oryzae* triose phosphate isomerase.

In particular when the host organism is *A. oryzae*, a preferred promoter for use in the process of the present invention is the *A. oryzae* TAKA amylase promoter as it exhibits a strong transcriptional activity in *A. oryzae.* The sequence of the TAKA amylase promoter appears in EP 238 023.

Termination and polyadenylation sequences may suitably be derived from the same sources as the promoter.

The techniques used to transform a fungal host cell may suitably be as described in EP 238 023.

To ensure secretion of the lipase A or the lipase variant from the host cell, the DNA sequence encoding the lipase variant may be preceded by a signal sequence which may be a naturally occurring signal sequence or a functional part thereof or a synthetic sequence providing secretion of the protein from the cell. In particular, the signal sequence may be derived from a gene encoding an Aspergillus sp. amylase or glucoamylase, a gene encoding a *Rhizomucor miehei* lipase or protease, or a gene encoding a Humicola cellulase, xylanase or lipase. The signal sequence is preferably derived from the gene encoding *A. oryzae* TAKA amylase, *A. niger* neutral α-amylase, *A. niger* acid-stable α-amylase or *A. niger* glucoamylase.

The medium used to culture the transformed host cells may be any conventional medium suitable for culturing Aspergillus cells. The transformants are usually stable and may be cultured in the absence of selection pressure. However, if the transformants are found to be unstable, a selection marker introduced into the cells may be used for selection.

The mature lipase protein secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

It will be understood that the lipase variants of the invention are contemplated to be active towards the same type of substrates as their parent lipases, with an improved specific activity. Thus, the lipase variants of the invention are contemplated to be useful for the same purposes as their parent lipases.

Accordingly, lipase variants of the invention prepared from a parent lipase useful as a detergent enzyme may be used as an active ingredient in a detergent additive or a detergent composition.

Another contemplated use of lipase variants of the invention, is as digestive enzymes, e.g. in the treatment of cystic fibrosis.

A third use of the lipase variants of the invention, especially variants of *C. antarctica* lipases are in lipase-catalysed processes such as in ester hydrolysis, ester synthesis and interesterification. The use of lipases in these processes is discussed in detail in WO 88/02775 (Novo Nordisk A/S), the content of which is incorporated herein by reference. Furthermore, as the *C. antarctica* is a nonspecific lipase, it may be used for randomization, e.g. in the preparation of margarine. Also the lipase variants of the invention may be used to avoid pitch trouble that arises in the production process for mechanical pulp or in a paper-making process using mechanical pulp, e.g. as described in PCT/DK92/00025 (Novo Nordisk A/S), the content of which is incorporated herein by reference.

BRIEF DESCRIPTION OF THE DRAWINGS

The present invention is described in the following with reference to the appended drawings, in which.

Figure 1:
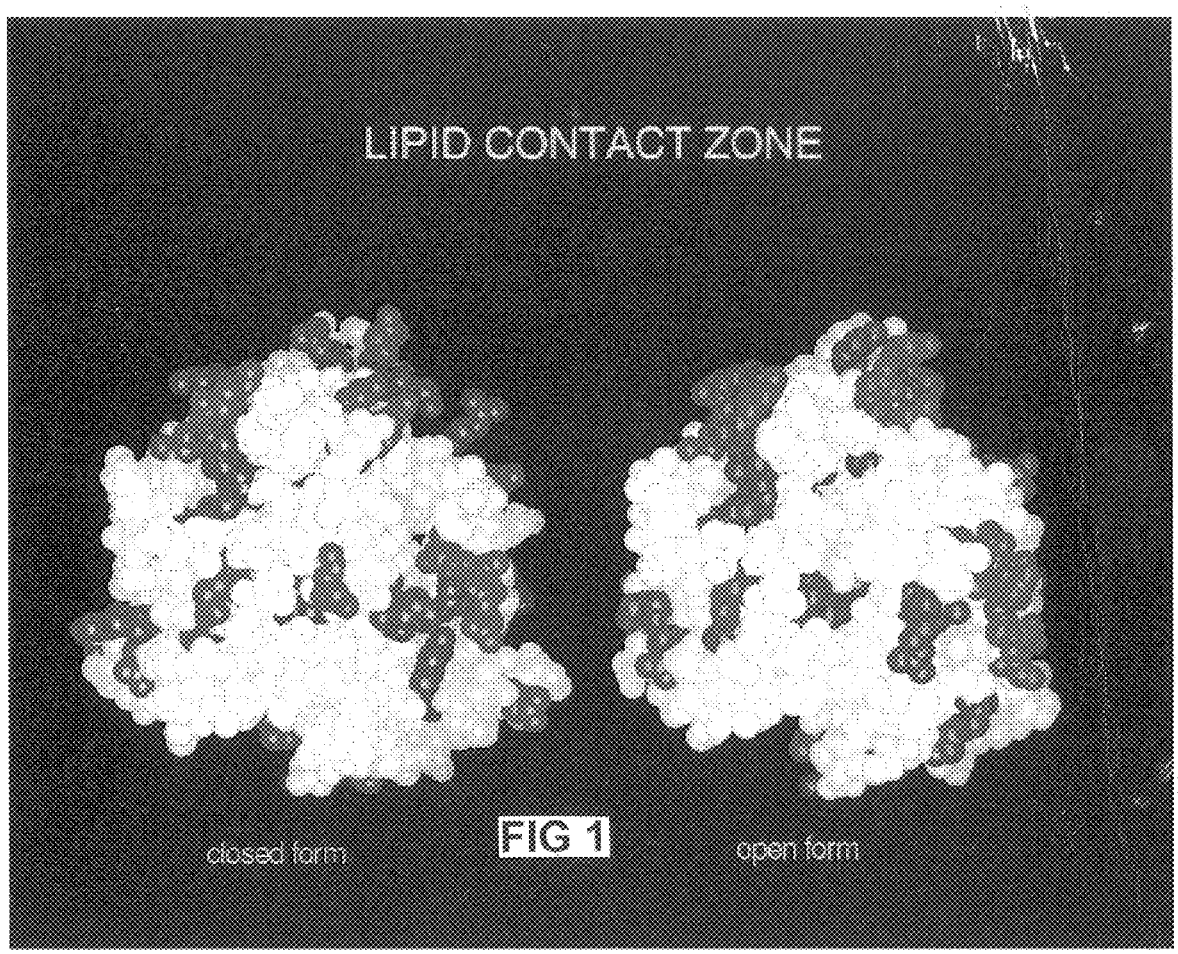
FIG. 1 is a computer model showing the three-dimensional structure of the lipid contact zone of the *H. lanuginosa* lipase described in WO 92/05249 when the lipase is in inactive (closed) and active (open) form, respectively. "White" residues represent hydrophobic amino acids (Ala, Val, Leu, Ile, Pro, Phe, Trp, Gly and Met), "yellow" residues represent hydrophilic amino acids (Thr, Ser, Gln, Asn, Tyr and Cys), "blue" residues represent positively charged amino acids (Lys, Arg and His), and "red" residues represent negatively charged amino acids (Glu and Asp).

The present invention is further illustrated in the following examples which are not intended, in any way, to limit the scope of the invention as claimed.

MATERIALS

Plasmids and Microorganisms
  pBoel777 (p777) (described in EP 0 489 718)
  p775 (the construction of which is described in EP 0 238 023)
  pIC19H (Marsh et al., Gene 32 (1984), pp. 481–485)
  pToC90 (described in WO 91/17243)
  *Aspergillus oryzae* A1560: IFO 4177
  *E. coli* MT172 (a K12 restriction deficient *E. coli* MC1000 derivative)

GENERAL METHODS

Site-Directed in Vitro Mutagenesis of Lipase Genes

The three different approaches described in WO 92/05249 may be used for introducing mutations into the lipase genes, i.e. the oligonucleotide site-directed mutagenesis which is described by Zoller & Smith, DNA, Vol. 3, No. 6, 479–488 (1984), the PCR method as described in Nelson & Long, Analytical Biochemistry, 180, 147–151 (1989), and the so-called "cassette mutagenesis" technique, in which a segment between two restriction sites of the lipase-encoding region is replaced by a synthetic DNA fragment carrying the desired mutation. Use of the latter technique is illustrated in Example 2.

Determination of Lipase Specific Activity

Lipase activity was assayed using glycerine tributyrat as a substrate and gum-arabic as an emulsifier. 1 LU (Lipase Unit) is the amount of enzyme which liberates 1 μmol titratable butyric acid per minute at 30° C., pH 7.0. The lipase activity was assayed by pH-stat using Radiometer titrator VIT90, Radiometer, Copenhagen. Further details of the assay are given in Novo Analytical Method AF 95/5, available on request.

EXAMPLES

Example 1

Cloning of *Candida antarctica* Lipase A

Chromosomal DNA of the *C. antarctica* strain LF058 (=DSM 3855 deposited with the Deutsche Sammlung von Mikroorganismen (DSM) on Sep. 29, 1986 under the terms of the Budapest Treaty, and further described in WO 88/02775) was prepared by opening of frozen cells by grinding with quartz and subsequent extraction of DNA essentially as described by Yelton et al., (1984). The purified DNA was cut partially with Sau3A and, after agarose gel electrophoresis, fragments in the range of 3–9 kb were isolated. The sized Sau3A fragments were ligated into a BamH1-cut, dephosphorylated plasmid pBR322 (New England Biolabs). The ligation mix was transformed into the *E. coli* MT172. Approximately 50,000 transformant *E. coli* colonies were obtained, 80% of which contained an insert of LF058 DNA.

Using standard colony hybridization techniques (Maniatis et al., 1982) the colonies were screened with the $32^P$-phosphorylated oligonucleotide probe NOR 440 (SEQ ID No. 7). NOR 440 is a degenerated (64) 17 mer based on the N-terminal determined from mature *C. antarctica* lipase A (SEQ ID No. 2). 34 colonies appeared positive after wash at low stringency (41° C. and 6×SSC). Plasmids were prepared from these colonies and Southern analyzed after restriction with BstNl. The probe for the Southern was either the NOR 440 probe (SEQ ID No. 7) used for the colony hybridization (see above) or a $32^P$-labelled probe NOR 438 (SEQ ID No. 6). NOR 438 is an oligonucleotide (a guess mer) where, at 13 positions, a base has been chosen on the basis of codon use in yeasts and filamentous fungi.

```
AACCCATACGACGACCC              NOR 440
   T C  T  T  T                (SEQ ID No. 7)
     G
     T

NOR 438
                               (SEQ ID No. 6)

GCTGCTCTGCCTAACCCTTACGACGACCCTTTCTACACCACCC
              T    T    T
``` guess positions indicated

Only one plasmid, pMT1076, contained a band which hybridized both to NOR 440 at low stringency (see above) and to NOR 438 at a somewhat higher stringency (55° C. and 1×SSC).

PMT1076 was restriction mapped and the DNA sequence determined by the Maxam-Gilbert method. The sequence covering the open reading frame is shown in SEQ ID No. 1. The open reading frame is seen to encode a putative signal sequence of 21 amino acids (according to the von Heine rules (von Heijne, G. (1986)) and furthermore a propeptide of 10 amino acids preceding the N-terminal of the mature lipase. The last two amino acids of the propeptide are Arg Arg, i.e. a typical cleavage site for endoproteolytic processing by enzymes of the *S. cereviciae* KEX-2 type. The amino acid composition of the mature protein (starting at position 32) encoded by the DNA sequence is in agreement with the amino acid composition determined for *C. antarctica* lipase A, cf. the following table:

TABLE I

Amino acid composition of *C. antartica* lipase A (CALIP)

|         | Deduced from DNA sequence | By amino acid analysis (MC) |
|---------|---------------------------|-----------------------------|
| Ala     | 50                        | 47                          |
| Arg     | 9                         | 9                           |
| Asp/AsN | 35                        | 36                          |
| Cys     | 4                         | 4                           |
| Gln/GlN | 35                        | 36                          |
| Gly     | 28                        | 31                          |
| His     | 6                         | 6                           |
| Ile     | 26                        | 24                          |
| Leu     | 29                        | 30                          |
| Lys     | 17                        | 17                          |
| Met     | 2                         | 3                           |
| Phe     | 20                        | 19                          |
| Pro     | 33                        | 33                          |
| Ser     | 26                        | 27                          |
| Thr     | 27                        | 28                          |
| Trp     | 5                         | 4                           |
| Tyr     | 18                        | 16                          |
| Val     | 27                        | 26                          |

Figure 2:
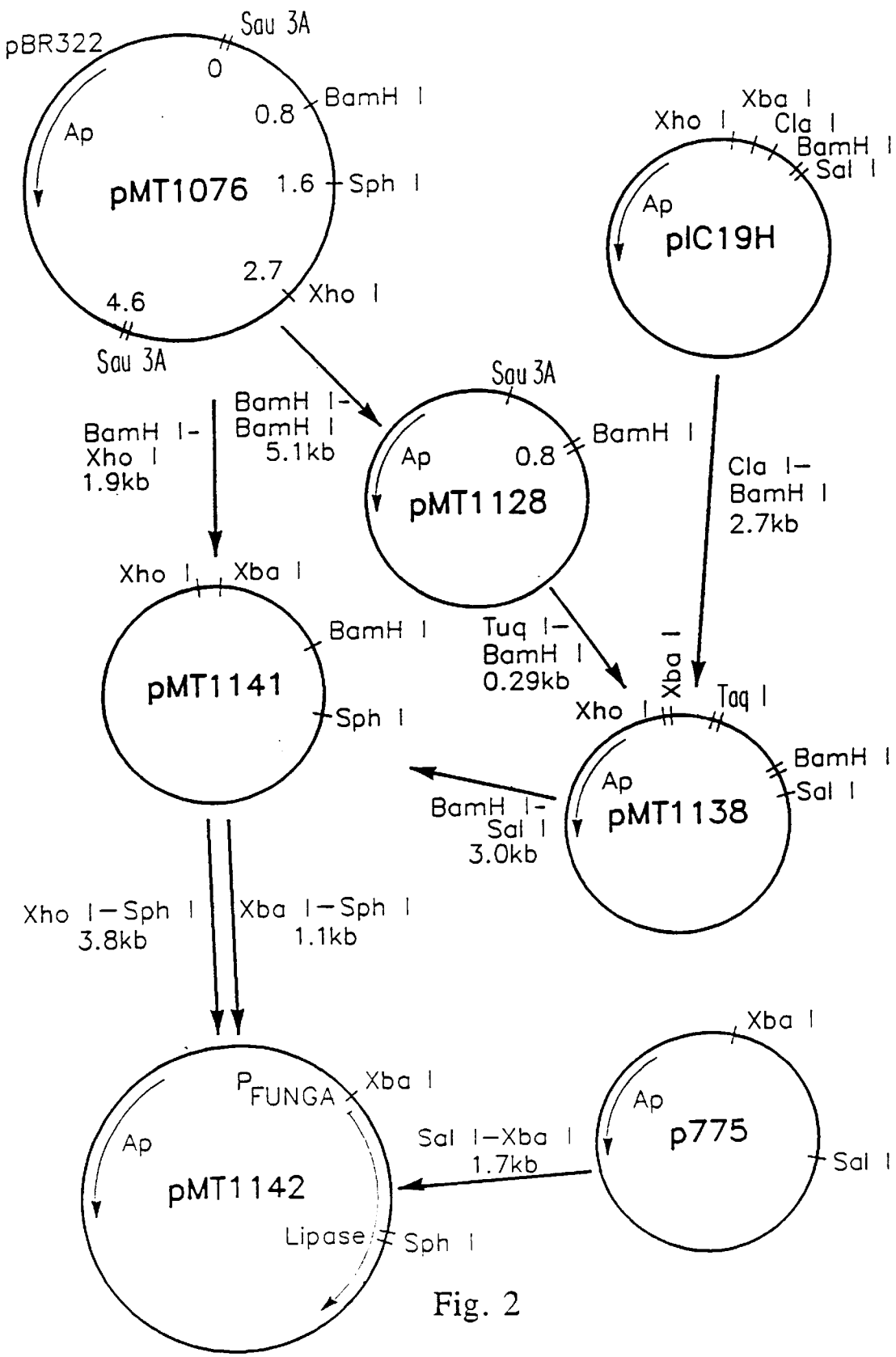
FIGS. 2 and 3 illustrate the scheme for the construction of the expression plasmid pMT1229 (see Example 1).
Figure 3:
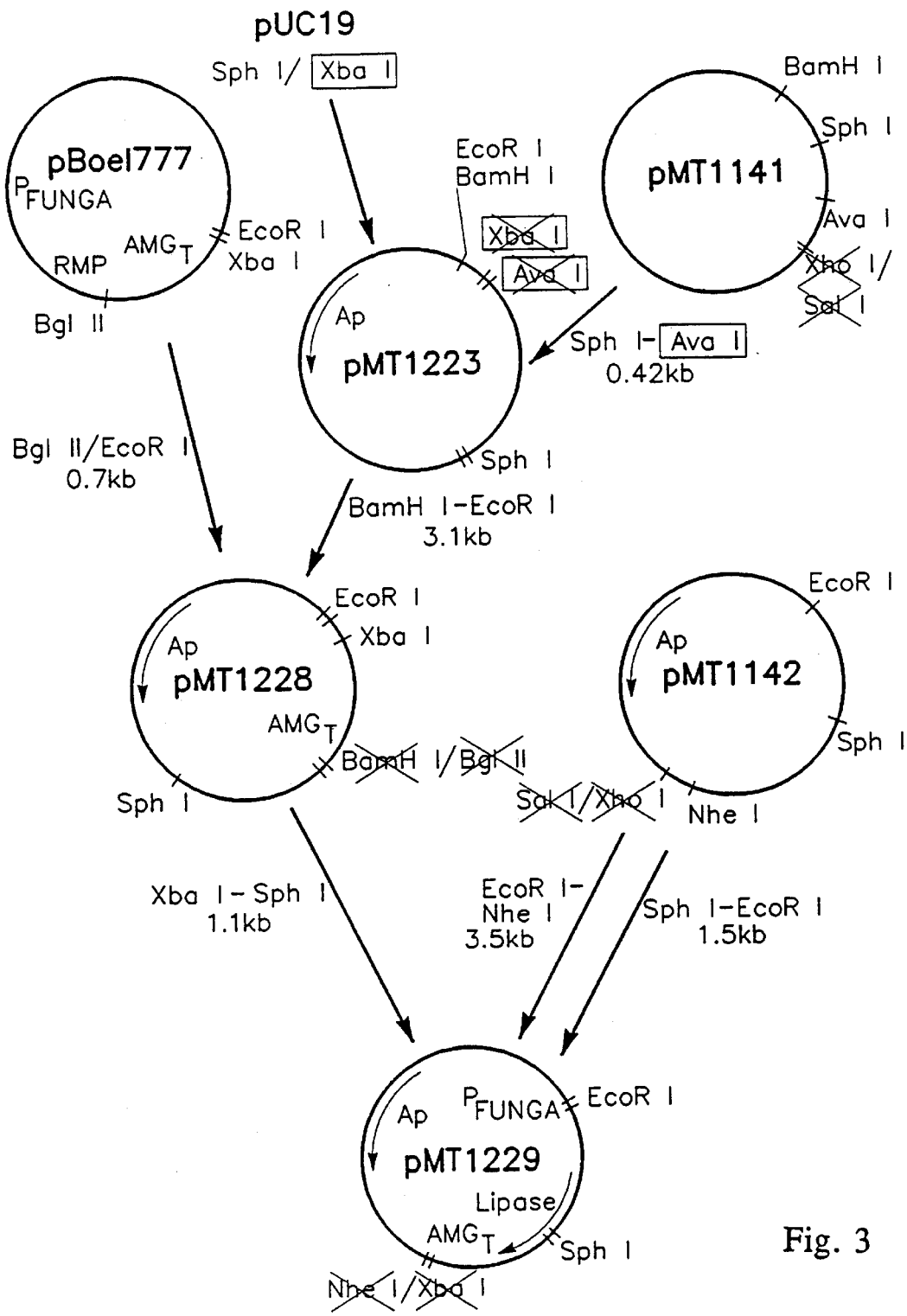

Through a number of standard plasmid manipulations (Maniatis et al., 1982) illustrated in FIGS. 2 and 3, the open reading frame of *C. antarctica* lipase A was placed in the correct orientation between the alpha-amylase promoter of *A. oryzae* and the glucoamylase transcription terminator of *A. niger*. The resulting expression plasmid pMT1229 was transformed into *A. oryzae* A1560 as described in EP 305, 216. Transformants were isolated and grown as described in the above cited patents and the culture supernatants were analyzed for the presence of *C. antarctica* lipase A.

Example 2
Construction of a Plasmid Expressing the F135W Variant of *Candida antarctica* Lipase A A 246 bp BamHI/BssHII fragment was synthesized in vitro on the basis of the nucleotide sequence of pMT1229 using oligonucleotide primers 3116 and 3117 in a PCR reaction. The primer 3117 includes a BssHII restriction site and a mutation in the 135 phe codon (TTC) to trp codon (TGG) which is marked with stars.

Oligonucleotide primer 3116 (F135W:256-276) (SEQ ID No. 8) 5'-CAG AAC GAG GCG GTG GCC GAC-3'

Oligonucleotide primer 3117 (F135W:566-487) (SEQ ID No. 9) 5'-TTC TTG AGC GCG CGG ATG CCG TCG AGG ATA GCC ATG CCC TCT TCG TAG CCA GCG ATG AAG GCG GCT TTC* C*AG CCT TCG TG-3'

The PCR reaction was performed by mixing the following components and incubating the mixture in a HYBAID™ thermal reactor.

| Template pMT1229 | 10 ng/μl | 1 μl |
|---|---|---|
| H₂O | | 46.5 μl |
| 10 × PCR buffer | | 10 μl |
| 2 mM dATP | | 10 μl |
| 2 mM dTTP | | 10 μl |
| 2 mM dCTP | | 10 μl |
| 2 mM dGTP | | 10 μl |
| primer 3116 | 50.5 pmol/μl | 1 μl |
| primer 3117 | 70.5 pmol/μl | 1 μl |
| Taq polymerase | | 0.5 μl |
| Parafin oil | | 50 μl |
| Step I    94° C. | 2 min. | 1 cycle |
| Step II   94° C. | 30 sec. | |
|           50° C. | 30 sec. | 30 cycle |
|           72° C. | 2 min. | |
| Step III  72° C. | 5 min. | 1 cycle |

The resulting 310 bp fragment was isolated from a 2% agarose gel after electrophoresis and digested with BamHI and BssHII restriction enzymes. The resulting 264 bp BamHI/BssHII fragment was likewise isolated from 2% agarose gel. This fragment was then ligated with

| pMT1229 | BamHI/XbaI | 0.3 kb |
|---|---|---|
| pMT1229 | BssHII/SphI | 0.5 kb |
| pMT1229 | SphI/XbaI | 5.0 kb |

The ligated DNA was transformed into *E. coli* strain MT172. Transformants which contained correct inserts were selected and their DNA sequence was determined by use of Sequenase (United States Biochemical Corporation). One resulting plasmid (pME-1178) contained a mutation in the amino acid position 135 (phe was mutated to trp).

pME1178 was cotransformed with pToC90 which included the amdS gene from *A. nidulans* as a selective marker into the *A. oryzae* A1560 strain using the procedure described in WO 91/17243. *A. oryzae* transformants were reisolated twice on selective plates and stable transformants were characterized by rocket immunoelectrophoresis, using anti-Candida lipase A antibody. Candida lipase A produced by a transformant (strain MEA65) was further analyzed for specific activity.

Example 3
Construction of a Plasmid Expressing the F139W Variant of *Candida antarctica* Lipase A A 246 bp BamHI/BssHII fragment was synthesized in vitro on the basis of the nucleotide sequence of the plasmid pMT1229 using oligonucleotide primers 3116 and 3826 in a PCR reaction. The primer 3826 includes a BssHII restriction site and a mutation in the 139 phe codon (TTC) to trp codon (TGG) which is marked with stars.

Oligonucleotide primer 3116 is shown in Example 2.

Oligonucleotide primer 3826 (F139W:566-487) (SEQ ID No. 10) 5'-TTC TTG AGC GCG CGG ATG CCG TCG AGG ATA GCC ATG CCC TCT TCG TAG CCA GCG ATC* C*AG GCG GCT TTG AAG CCT TCG TG-3'

A PCR reaction was performed by the method described in Example 2. The 310 bp fragment was isolated from 2% agarose gel after electrophoresis and digested by BamHI and BssHII restriction enzymes. The resulting 264 bp BamHI/BssHII fragment was likewise isolated from 2% agarose gel. This fragment was then ligated with

| pMT1229 | BamHI/XbaI | 0.3 kb |
|---------|------------|--------|
| pMT1229 | BssHII/SphI | 0.5 kb |
| pMT1229 | SphI/XbaI | 5.0 kb |

The ligated DNA was transformed into E. coli strain MT172. Transformants which contained correct inserts were selected and their DNA sequence was determined by use of Sequenase (United States Biochemical Corporation). One resulting plasmid (pME-1229) contained a mutation in the amino acid position 139 (phe was mutated to trp).

pME1229 was cotransformed with pToC90 which included the amdS gene from A. nidulans as a selective marker into A. oryzae A1560 strain. A oryzae transformants were reisolated twice on selective plates and enzyme activity of a stable transformant (MEA155) was analyzed by using tributylene as a substrate as described in Example 5.

Example 4

Construction of a Plasmid Expressing the F135W/F139W Variant of Candida antarctica Lipase A A 246 bp BamHI/BssHII fragment was synthesized in vitro using oligonucleotide primers 3116 and 4224 by a PCR reaction. The primer 4224 includes a BssHII restriction site and mutations in the 135 and 139 codons (TTC) to trp codons (TGG) which are marked with stars.

The oligonucleotide primer 3116 is shown in Example 2.

Oligonucleotide primer 4224 (F135W:566-487) (SEQ ID No. 11) 5'-TTC TTG AGC GCG CGG ATG CCG TCG AGG ATA GCC ATG CCC TCT TCG TAG CCA GCG ATC* C*AG GCG GCT TTC* C*AG CCT TCG TG-3'

PCR reaction was performed by using the method shown in Example 2. The 310 bp fragment was isolated from a 2% agarose gel after electrophoresis and digested with BamHI and BssHII restriction enzymes. The resulting 264 bp BamHI/BssHII fragment was likewise isolated from a 2% agarose gel. This fragment was then ligated with

| pMT1229 | BamHI/XbaI | 0.3 kb |
|---------|------------|--------|
| pMT1229 | BssHII/SphI | 0.5 kb |
| pMT1229 | SphI/XbaI | 5.0 kb |

The ligated DNA was transformed into E. coli MT172. Transformants which contained inserts were selected and their DNA sequence was determined by use of Sequenase. One resulting plasmid (pME1230) contained two mutations in the amino acid positions 135 and 139 (phe was mutated to trp).

pME1230 was cotransformed with pToC90 which included the amds gene from A. nidulans as a selective marker into A. oryzae A1560 strain. A. oryzae transformants were reisolated twice on selective plates and enzyme activity of stable transformants were analyzed by using tributylene as a substrate as described in Example 5.

Example 5

Purification of C. antarctica Lipase A Variants P139W and F135W/F139W and Comparison of Specific Activity with their Parent Wild Type C. antarctica Lipase A The lipase variants and the parent lipase produced as described in Examples 3, 4 and 1, respectively, were purified using the following 4 step standard purification procedure.

Step 1: The fermentation broth containing the lipase and lipase variant, respectively, obtained by culturing the transformed A. oryzae cells described in Examples 1 and 3 above, was centrifuged, and the supernatant was adjusted to pH 7. Ionic strength was adjusted to 2 mSi. DEAE-Sephadex A-50 (Pharmacia) gel was swollen and equilibrated in 25 mM Tris acetate buffer pH 7. The fermentation supernatant was passed through DEAE-Sephadex A-50 on scintered glass funnel. The effluent containing lipase activity was collected and adjusted to 0.8 M ammonium acetate.

Step 2: An appropriate column was packed with TSK gel Butyl-Toyopearl 650 C and equilibrated with 0.8 M ammonium acetate. The effluent containing lipase activity was applied on the column. The bound material was eluted with water.

Step 3: The lipase-containing eluate was then applied on a Highperformance Q-Sepharose column. Lipase activity was collected as effluent. The lipases purified by this method were concentrated to an Optical Density of 1 at 280 nm.

The purity of the lipases was checked by SDS-PAGE showing one band with an molecular weight of about 45 kD. The lipase activity was determined by use of the method outlined above in the section "General methods".

The lipase activity of the parent wild type lipase was 300 LU/OD$_{280}$ as compared to 1200 LU/OD$_{280}$ for the lipase variant F139W. On the basis of OD$_{280}$ absorption without correction for the inserted tryptophan, the specific activity of the mutant was at least four times higher with the assay used. The lipase activity of the lipase variant F135W/F139W was 1400 LU/OD$_{280}$ (without correction for the two additional tryptophans).

Example 6

Thermostability of Candida antarctica Lipase A and the Mutant F139W thereof

The thermostability of the C. antarctica lipase A and the C. antarctica lipase A variant, was examined by Differential Scanning Calorimetry (DSC) at different pH values. Using this technique, the thermal denaturation temperature, $T_d$, is determined by heating an enzyme solution at a constant programmed rate.

More specifically, the Differential Scanning Calorimeter, MC-2D, from MicroCal Inc. was used for the investigations. Enzyme solutions were prepared in 50 mM buffer solutions, cf. the tables below. The enzyme concentration ranged between 0.6 and 0.9 mg/ml, and a total volume of about 1.2 ml was used for each experiment. All samples were heated from 25° C. to 90° C. at a scan rate of 90° C./hr.

The results obtained from the analysis is shown in the table below:

| pH | Buffer (50 mM) | Denaturation temperature[1] |
|----|----------------|-----------------------------|
| C. ant. lipase A (WT) | | |
| 4.5 | Acetate | 96° C. |
| 5 | Acetate | 95° C. |
| 7 | TRIS | 93° C. |

-continued

| pH | Buffer (50 mM) | Denaturation temperature[1] |
|---|---|---|
| | C. ant. lipase A mutant (F139W) | |
| 5 | Acetate | 84° C. |
| 7 | TRIS | 82° C. |

[1]Temperature, at which approximately half the enzyme molecules present have been denatured thermally during heating The above results show that the pH-optimum for the thermostability of C. antarctica lipase A and the F139W variant is unusually low and that both enzymes are very thermostable below pH 7. Within the investigated range the thermostability of both the Wild Type and the mutant F139W continues to increase as pH is lowered. This makes both lipases very well suited for hydrolysis/synthesis at unusually high temperatures at relatively low pH values.

References Cited in the Application

Winkler, F. K. et al., (1990), Structure of Human Pancreatic Lipase. Nature, vol. 343, 771–774,
Schrag, J. D. et al., (1991), Ser-His-Glu triad Forms the Catalytic Site of the Lipase from Geotrichum candidum. Nature, vol. 351, 761–764,
Brady, Leo et al., (1990), A Serine Protease Triad Forms the Catalytic Centre of a Triacylglycerol Lipase. Nature, vol 343, 767–770,
Brzozowski, A. M. et al., (1991), A Model for Interfacial Activation in Lipases from the Structure of a Fungal Lipase-inhibitor Complex. Nature, vol. 351, 491–494,
Derewenda, Urszula et al., (1992), Catalysis at the Interface: The Anatomy of a Conformational Change in a Triglyceride Lipase. Biochem., 31, 1532–1541,
Tilbeurgh et al., Nature, Vol. 362, 814–820, (1993)
Komaromy, M. C. et al., (1987), Cloning of Rat Hepatic Lipase cDNA: Evidence for a Lipase Gene Family. Proc.Natl.Acad.Sci., 84, 1526–1530,
Datta, S. et al., (1988) Human Hepatic Lipase. J.Biol.Chem., 263, 1107–1110,
Bodmer, M. W. et al., (1987) Molecular Cloning of a Human Gastric Lipase and Expression of the Enzyme in Yeast. Biochimica et Biophysica Acta, 909, 237–244.
Baba, T. et al., (1991), Structure of Human Milk Bile Salt Activated Lipase. Biochemistry, 30, 500–510,
Grusby, M. J. et al., (1990), Cloning of an Interleukin-4 Inducible Gene from Cytotoxic T Lymphocytes and its Identification as a lipase. Cell 60, 451–459,
Caro, J. De. et al., (1981) Porcine Pancreatic Lipase. Completion of the Primary Structure. Biochim.Biophys. Acta 671, 129–138,
Lowe, M. E. et al., (1989), Cloning and Characterization of Human Pancreatic Lipase cDNA. J.Biol.Chem., 264, 20042–20048,
Mickel, F. S. et al., (1989), Structure of the Canine Pancreatic Lipase Gene. J.Biol.Chem., 264, 12895–12901,
S. L. Beaucage and M. H. Caruthers, Tetrahedron Letters 22, 1981, pp. 1859–1869,
Matthes et al., The EMBO J. 3, 1984, pp. 801–805
R. K. Saiki et al., Science 29, 1988, pp. 487–491
Morinaga et al., 1984, Biotechnology 2: 646–639
Nelson and Long, Analytical Biochemistry 180, 1989, pp. 147–151
Villa-Kamaroff, et al., 1978, Proc. Natl. Acad. Sci. U.S.A. 75: 3727–3731)
DeBoer, et al., 1983, Proc. Natl. Acad. Sci. U.S.A. 80: 21–25
"Useful proteins from recombinant bacteria" in Scientific American, 1980, 242: 74–94.
Marsh et al., Gene 32 (1984), pp. 481–485)
Docherty, A. J. P. et al., (1985), Molecular Cloning and Nucleotide Sequence of Rat Lingual Lipase cDNA. Nucleic Acids Research, 13, 1891–1903,
Maniatis, T. et al., Molecular Cloning, Cold Spring Harbor, 1982,
Sambrook et al., Molecular Cloning: A Laboratory Manual, 2nd Ed., Cold Spring Harbor, 1989,
Zoller & Smith, DNA, Vol. 3, No. 6, 479–488 (1984),
Nelson & Long, Analytical Biochemistry, 180, 147–151 (1989)
von Heijne, G. Nucl. Acid. Res. 14 (1986), pp. 4683–90,
Yelton et al., PNAS 81 (1984), pp. 1470–74,
Aoyama, S. et al., (1988), Cloning, sequencing and expression of the lipase gen from Pseudomonas fragi IFO-12049 in E. coli. FEBS Lett., 242, 36–40,
Derewenda, Zygmunt S. et al., (1992), Relationships Among Serine Hydrolases: Evidence for a Common Structural Motif in Triacylglyceride Lipases and Esterases,

We claim:

1. A lipase variant comprising a modification in an amino acid sequence of a parent lipase having the amino acid sequence of SEQ ID NO:2, wherein the modification is the substitution of phenylalanine at position 139 of the mature lipase (position 170 of SEQ ID NO:2) with tryptophan.

2. A lipase variant comprising a modification in an amino acid sequence of a parent lipase having the amino acid sequence of SEQ ID NO:2, wherein the modification is the substitution of phenylalanine at positions 135 and 139 of the mature lipase (positions 166 and 170 of SEQ ID NO:2) with tryptophan.

3. A lipase variant comprising a modification in an amino acid sequence of a parent lipase having the amino acid sequence of SEQ ID NO:3, wherein the modification is the substitution of phenylalanine at position 29 with trypophan.

4. A lipase variant comprising a modification in an amino acid sequence of a parent lipase having the amino acid sequence of SEQ ID NO:5, wherein the modification is the substitution of alanine at position 117 with tryptophan.

5. A DNA construct comprising a DNA sequence encoding a lipase variant according to claim 1.

6. A recombinant expression vector which carries a DNA construct according to claim 5.

7. A host cell which is transformed with a DNA construct according to claim 5.

8. A method of producing a lipase variant, comprising
(a) culturing a host cell according to claim 7 under conditions conducive to the production of the lipase variant and
(b) recovering the lipase variant from the culture.

9. An enzymatic process, comprising
(a) reacting an ester with water;
(b) reacting an acid with an alcohol; or
(c) reacting an ester with an acid, an alcohol or a second ester, wherein the reaction is catalyzed by a lipase variant according to claim 1.

10. A process for hydrolyzing resin in pulp, comprising hydrolyzing the pulp with a lipase variant according to claim 1.

11. A DNA construct comprising a DNA sequence encoding a lipase variant according to claim 2.

12. A recombinant expression vector which carries a DNA construct according to claim 11.

13. A host cell which is transformed with a DNA construct according to claim 11.

14. A method of producing a lipase variant, comprising
(a) culturing a host cell according to claim 13 under conditions conducive to the production of the lipase variant and (b) recovering the lipase variant from the culture.

15. An enzymatic process, comprising
   (a) reacting an ester with water;
   (b) reacting an acid with an alcohol; or
   (c) reacting an ester with an acid, an alcohol or a second ester, wherein the reaction is catalyzed by a lipase variant according to claim 2.

16. A process for hydrolyzing resin in pulp, comprising hydrolyzing the pulp with a lipase variant according to claim 2.

17. A DNA construct comprising a DNA sequence encoding a lipase variant according to claim 3.

18. A recombinant expression vector which carries a DNA construct according to claim 17.

19. A host cell which is transformed with a DNA construct according to claim 17.

20. A method of producing a lipase variant, comprising
   (a) culturing a host cell according to claim 19 under conditions conducive to the production of the lipase variant and
   (b) recovering the lipase variant from the culture.

21. An enzymatic process, comprising
   (a) reacting an ester with water;
   (b) reacting an acid with an alcohol; or
   (c) reacting an eater with an acid, an alcohol or a second ester, wherein the reaction is catalyzed by a lipase variant according to claim 3.

22. A process for hydrolyzing resin in pulp, comprising hydrolyzing the pulp with a lipase variant according to claim 3.

23. A DNA construct comprising a DNA sequence encoding a lipase variant according to claim 4.

24. A recombinant expression vector which carries a DNA construct according to claim 23.

25. A host cell which is transformed with a DNA construct according to claim 23.

26. A method of producing a lipase variant, comprising
   (a) culturing a host cell according to claim 25 under conditions conducive to the production of the lipase variant and
   (b) recovering the lipase variant from the culture.

27. An enzymatic process, comprising
   (a) reacting an ester with water;
   (b) reacting an acid with an alcohol; or
   (c) reacting an ester with an acid, an alcohol or a second ester, wherein the reaction is catalyzed by a lipase variant according to claim 4.

28. A process for hydrolyzing resin in pulp, comprising hydrolyzing the pulp with a lipase variant according to claim 4.

* * * * *